United States Patent
Skurka et al.

[11] Patent Number: 5,836,919
[45] Date of Patent: Nov. 17, 1998

[54] CAP ASSEMBLY

[75] Inventors: Gregory Skurka, Chicago, Ill.; Clinton A. Haynes, West Chester; Douglas Marriott, South Lebenon, both of Ohio

[73] Assignee: Solopak Pharmaceuticals, Inc., Elk Grove Village, Ill.

[21] Appl. No.: 814,099

[22] Filed: Mar. 10, 1997

Related U.S. Application Data

[63] Continuation of Ser. No. 652,151, May 23, 1996, abandoned.

[51] Int. Cl.⁶ .................................................... A61M 5/00
[52] U.S. Cl. ........................... 604/187; 604/227; 604/243
[58] Field of Search .................................. 604/187, 218, 604/227, 232, 240–243

[56] References Cited

U.S. PATENT DOCUMENTS

| | | |
|---|---|---|
| 791,802 | 6/1905 | De Lisle . |
| 2,266,270 | 12/1941 | Roth . |
| 2,481,636 | 9/1949 | Willis . |
| 2,727,651 | 12/1955 | Mickelson . |
| 3,108,592 | 10/1963 | Hassing et al. ..................... 604/232 X |
| 3,803,700 | 4/1974 | Tischlinger . |
| 3,847,183 | 11/1974 | Meyer . |
| 3,885,297 | 5/1975 | Tischlinger . |
| 3,978,858 | 9/1976 | Tischlinger .......................... 604/227 X |
| 3,987,940 | 10/1976 | Tischlinger .......................... 604/227 X |
| 4,291,695 | 9/1981 | Bekkering et al. .................. 604/227 X |
| 5,135,514 | 8/1992 | Kimber . |
| 5,139,490 | 8/1992 | Vetter et al. . |
| 5,224,515 | 7/1993 | Foster et al. . |
| 5,509,903 | 4/1996 | Grendahl et al. ........................ 604/187 |

*Primary Examiner*—John D. Yasko
*Attorney, Agent, or Firm*—Banner & Witcoff Ltd.

[57] ABSTRACT

The present invention relates to an inventive non-elastomeric thermoplastic cap assembly that may be secured on an end of a generally cylindrical body at room temperatures. The cap is a deformable tubular sheath having an interior surface, an exterior surface, a first open end for receiving the end of the cylindrical body, and a second end which is at least partially closed to inhibit passage of the cylindrical body through the second end. The sheath has a gripping region adjacent the first open end to engage the exterior surface of the cylindrical body. The gripping region may include at least one ridge on the interior surface of the tubular sheath. The sheath also has a transition region adjacent the second end of the sheath, which helps the sheath provide a controlled and predictable amount of retention force over a wide range of component tolerances.

25 Claims, 4 Drawing Sheets

FIG. 4
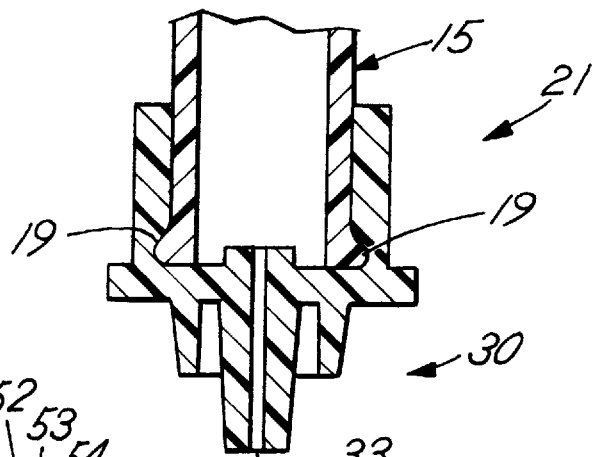
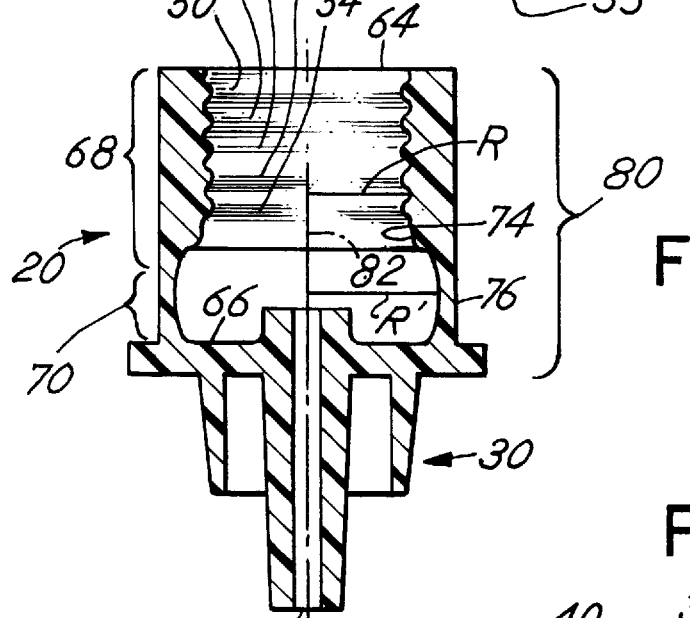
FIG. 5a
FIG. 5b
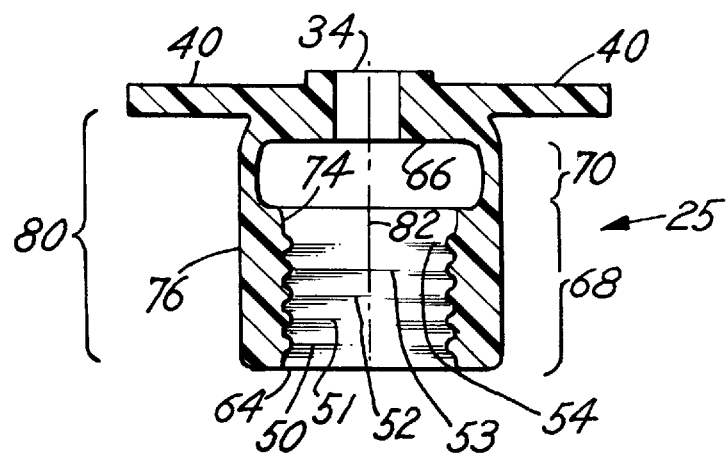

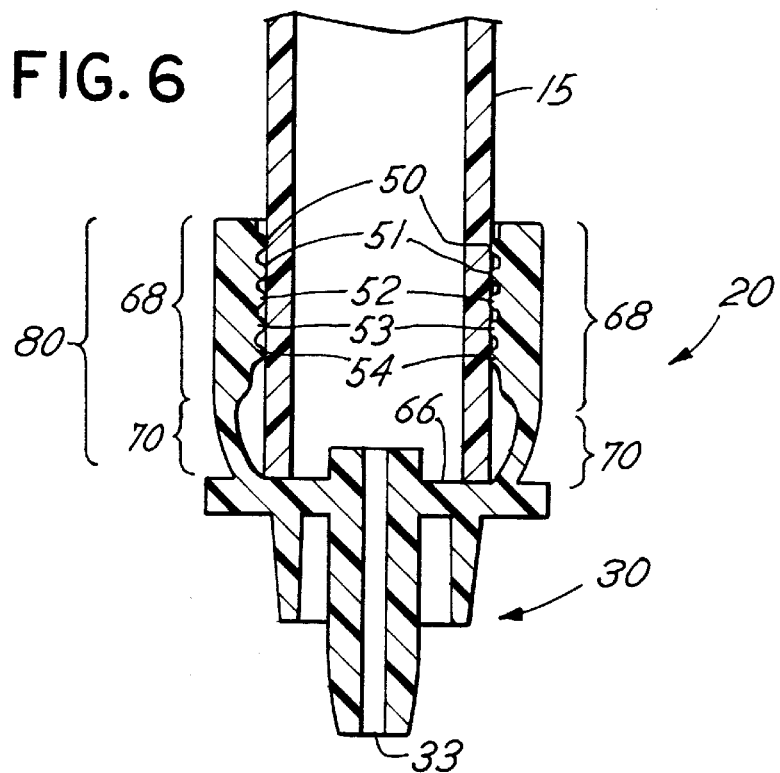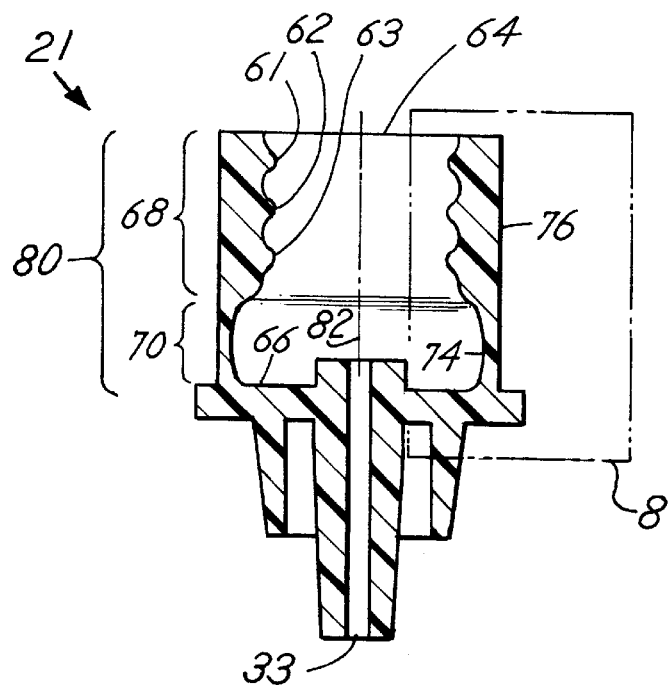

CAP ASSEMBLY

This application is a continuation of application Ser. No. 08/652,151, filed May 23, 1996, now abandoned.

BACKGROUND OF THE INVENTION

The present invention relates to a cap assembly for an end of a generally cylindrical body. Indeed, the cap assembly of the present invention is particularly useful in connection with a syringe having a cylindrical tube which forms the central body of the syringe.

Syringes are commonly formed from a combination of parts, including both plastic and glass components. An open-ended glass tube generally forms the central body portion of the syringe, and may serve as a medicant reservoir. The glass tube provides a clear and chemically inert container for drugs and other chemicals which may be held by the syringe.

The open ends of the central body portion of a syringe of this sort may typically terminate with plastic cap members. The cap at a first end of the syringe central body may provide support for a plunger. Such a cap is often called the flange. The cap at the other end of the central body is generally referred to as the tip. The tip may incorporate a standard connection to the LUER fitting used in medical dispensing devices. Both the flange and the tip may be generally identical in construction and function in terms of terminating the central body portion of the syringe.

In order to manufacture syringes of the type described above, there must be a means for securing the cap members to the respective ends of the cylindrical body. The caps must be sufficiently secured to withstand various forces that may be exerted on the caps, including forces generated when the plunger is depressed.

One method by which the caps may be secured to the tube is through the use of an adhesive. The use of adhesives, however, often result in an assembly process that is slow, complex, and messy. Moreover, there exists the potential that the adhesive may inadvertently come into contact with the drug or other liquid chemical stored in the syringe central body, which could jeopardize the purity of the retained drug or compound. FDA approval of adhesives can be time consuming and costly.

While an insert molding process may alternatively be used to form a plastic member on to a glass tube, such insert molding processes typically require very close tolerance controls. Such close tolerance controls may not be readily available when commercially available glass tubing is used. Glass tubing of this sort typically is supplied with fairly wide tolerance variation.

Arrangements in which threaded caps cooperate with threaded ends of the glass tube increases manufacturing costs, and also raises the potential for undue stress conditions which may, in turn, lead to tip or end fracture. Further, such an arrangement again generally requires close tolerance controls to insure an effective seal.

It is also possible to construct a positive key arrangement, whereby a glass bead formed around the circumference at the end of the glass tube cooperates with the plastic cap to retain the plastic cap. Positive keying, however, calls for additional steps in the glass tube manufacturing process, which in turn adds to both the cost and the reliability of the glass tube. It is more difficult to control the dimensions of glass tube cut-offs and beads during manufacturing. Further, it is generally necessary to apply heat to plastic caps during assembly of the caps over beads formed at the end of glass tubes having diameter variations.

Another option is to provide a tight frictional fit between the cap and the cylindrical glass body. The frictional force generated between the plastic cap and tube interface retains the cap on the tube with a predetermined amount of pull-off force. Frictional retention caps of this sort, however, do not generally provide sufficient control and predictability over the retention force for a wide range of component tolerances.

It is therefore an object to the present invention to provide a cap assembly that provides control and predictability over the resulting retention forces for a wide range of component tolerances. It is also an object of the present invention to provide a cap assembly that may be secured in place at room temperatures without the application of any external heat. Other objects of the present invention will be apparent by the following description.

SUMMARY OF THE INVENTION

The inventive cap assembly relates to a non-elastomeric thermoplastic cap that may be secured on a smooth end of a generally cylindrical body at room temperatures. The cap has a deformable tubular sheath with an interior surface, an exterior surface, a first open end for receiving the end of said cylindrical body, and a second end which is at least partially closed to inhibit passage of the cylindrical body through the second end. The sheath has a gripping region adjacent the first open end, and a transition region adjacent the second end of the sheath. The gripping region engages the exterior surface of the cylindrical body. The gripping region may include at least one ridge on the interior surface of the tubular sheath, extending radially inward toward a central axis of the sheath and around the circumference of the interior surface of the sheath. The sheath is deformable upon interaction of the cylindrical body and the gripping region of the sheath. The transition region, which extends between the second end of the sheath and the gripping region, has an inside radius that is greater than the inside radius of the undeformed gripping region. The transition region helps to provide a controlled and predictable variation of stress in the transition from stretched to unstretched regions over a wide range of component tolerances.

Such control and predictability is beneficial for a variety of reasons, including that it helps establish and guarantee a minimum required force before the cap can be removed by internal pressure. Such control and predictability also keeps the assembly force within close bounds. This in turn provides for a more reliable and higher-speed assembly, insofar as large variations in assembly force can lead to assembly problems such as jamming of the assembly machine when the interference between the cap and the tube is too large.

BRIEF DESCRIPTION OF THE DRAWING

A preferred embodiment of the present invention is described herein with reference to the drawing, wherein:

FIG. 4 is a cross-sectional view of an example prior art friction-fit end cap disposed on the end of a central body of a syringe, the end of the central body having a bead around the circumference and the end cap having a recess on the inside wall to receive the bead at the end of the central body in a positive-key relationship;

FIG. 5a is a cross-sectional view of the lower cap shown in FIG. 1;

FIG. 5b is a cross-sectional view of the upper end cap shown in FIG. 1;

FIG. 6 is a cross-sectional view of a lower cap for a syringe in accordance with one embodiment of the present invention, with a cylindrical body disposed therein;

FIG. 7 is a cross-sectional view of a lower cap for a syringe in accordance with a second embodiment of the present invention;

DESCRIPTION OF THE PREFERRED EMBODIMENT

Figure 1:
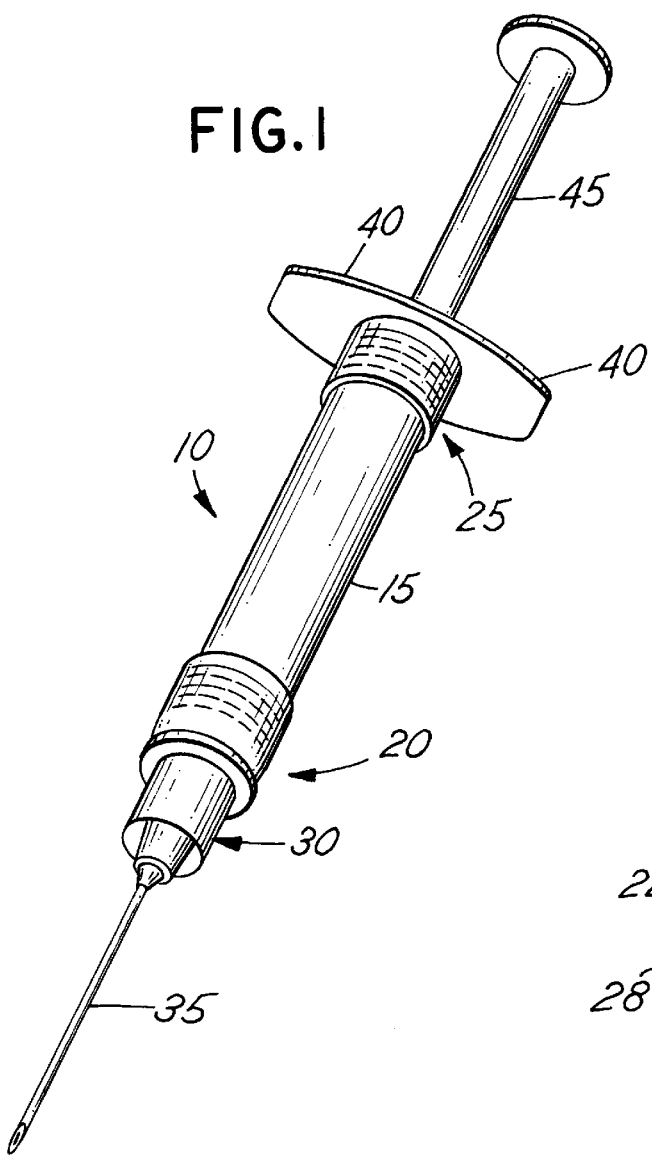
FIG. 1 is a perspective view of a syringe having end caps disclosing one embodiment of the present invention.

Referring now in detail to the various figures of the drawing, there is shown a cap assembly embodiment of the present invention for use as a component of a syringe 10. The syringe 10 may be adapted to provide a sterile barrier for certain medical applications. The syringe 10 includes a cylindrical glass tube 15 which forms the central body of the syringe 10. Glass tube 15 may be formed in a conventional manner by a die-formed melt process to create a generally smooth-surfaced cylindrical glass tube, which may subsequently be cut into sections to form desired lengths of glass tubing. If desired, the resultant glass tubing may be coated on its outer surface with, for example, silicone.

The lower end of the glass tube 15 is terminated with a tip member such as lower cap 20. Lower cap 20 may include a dispensing section such as necked down portion 30 that is configured in a conventional manner to cooperate with a needle portion 35 of the syringe 10. Needle conduit 33 accepts the needle 35 and permits passage of the retained fluid from the central body 15 through the needle 35.

The upper end of glass tube 15 terminates with a flange member such as upper cap 25. Upper cap 25 may include finger grip portions 40 to provide support for the operator's fingers while the plunger 45 is translated to inject fluid from or withdraw fluid into the glass tube portion 15 of the syringe 10. Plunger aperture 34 of upper cap 25 cooperates with the plunger 45 in a conventional manner.

Figure 2:
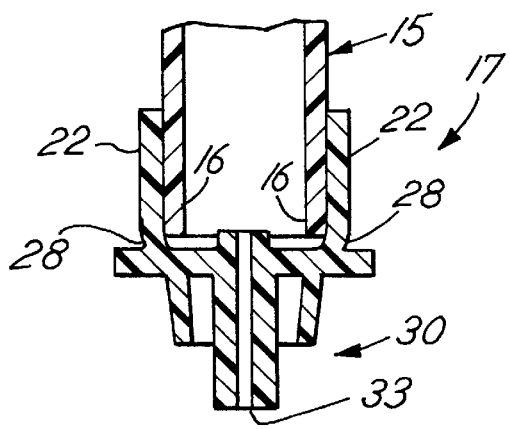
FIG. 2 is a cross-sectional view of an example prior art friction-fit end cap disposed on the end of a central body of a syringe, the cylinder walls at the end of the central body being generally smooth on the exterior surface.
Figure 3:
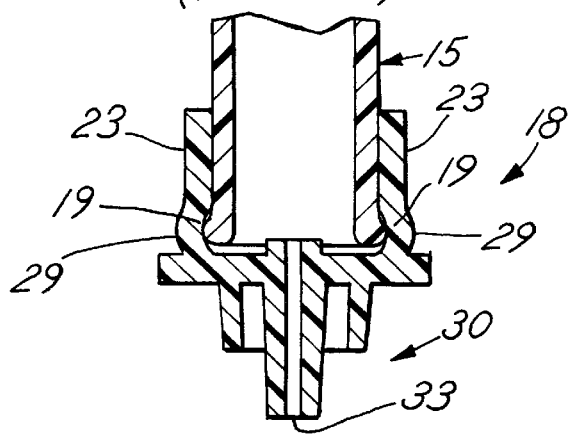
FIG. 3 is a cross-sectional view of an example prior art friction-fit end cap disposed on the end of a central body of a syringe, the end of the central body having a bead around the circumference.

Two prior art methods for securing caps to an end of a cylindrical body are shown for example in FIGS. 2 and 3. FIG. 2 illustrates a cap 17 having a cylindrical wall 22 that is straight and uniform in thickness. This stiff polymeric cap 17 is retained simply by the interference fit created between the cap 17 and the generally smooth wall 16 of the tube 15.

One of the problems which can arise with this style of cap is that a discontinuity in the cap 17 may form as a result of the increased stresses and/or strains generated by variances in the tolerances of the tube 15. These severe strains may result in undesirable cracking, crazing, or discoloration at, for example, at location 28.

Unwanted discontinuities similarly may occur, for example, at location 29 on wall 23 of cap 18, shown in FIG. 3. FIG. 3 illustrates an alternative prior art method for securing the cap to the tube 15. In this method, the wall 23 of cap 18 engages the bead 19 formed at the end of the tube 15. The interaction of the wall 23 with the bead 19 in turn helps secure the cap 18 to the tube 15. Such an arrangement, however, can lead to increased tubing costs and decreased predictability in the tube dimensions, insofar as it is typically more difficult to control the dimensions of glass tube cut-offs and beads during manufacturing.

FIG. 4 shows another alternative prior art method wherein the inside wall of cap 21 includes a recess to receive and engage the bead 19 formed at the end of the tube 15. This positive-key relationship relies at least in part on the bead 19 of the tube 15 to help secure the cap 21 in place. As described above, however, certain manufacturing problems and increased costs can be encountered with a cap design that relies at least in part on a bead at the end of the cylindrical body, as opposed to a generally smooth-ended cylindrical body similar to that which is shown for example in FIG. 2.

FIGS. 5a, 5b, and 6 illustrate in greater detail the preferred embodiments of the inventive lower cap 20 and upper cap 25 shown in FIG. 1. While preferred caps 20 and 25 are disposed on opposite ends of the central body 15 and cooperate with different syringe components, for the purposes of this disclosure they are essentially the same in terms of construction and function. Both caps 20 and 25 are similarly designed to fit over the ends of tube 15 to terminate the ends of the tube 15. Both caps 20 and 25 are secured to the tube 15 through a precision interference fit.

The caps of the present invention generally comprise a deformable tubular sheath portion 80 having a central axis 82, an interior surface 74, and an exterior surface 76. A first end 64 of the sheath 80 is open to receive an end of the cylindrical body 15 along the central axis 82. A second end 66 of the sheath 80 is at least partially closed, and may function at least in part to inhibit passage of the cylindrical body 15 through the second end 66 of the sheath 80. The sheath 80 has a substantially uniform outside diameter extending from the first end 64 to the second end 66.

The deformation of the sheath 80 caused by insertion of the cylindrical body helps provide the ring tension that generates the interfacial compressive force, or frictional resistance, between the cap and the cylindrical body 15. This engagement between the cap and the cylindrical body 15 secures the cap on the cylindrical body 15. The amount of force required to overcome the resulting interfacial compressive force between the cap and the cylindrical body 15 is generally referred to as the pull-off force associated with the interference fit.

As is shown in the figures and described above, the second end 66 and/or the exterior surface of the sheath 80 may be adapted for a particular use, such as to cooperate with either a needle 35 or a plunger 45 of a syringe 10. Other adaptations to the cap assembly which are suitable for particular applications will be readily apparent to those of ordinary skill in the art.

Figure 8:
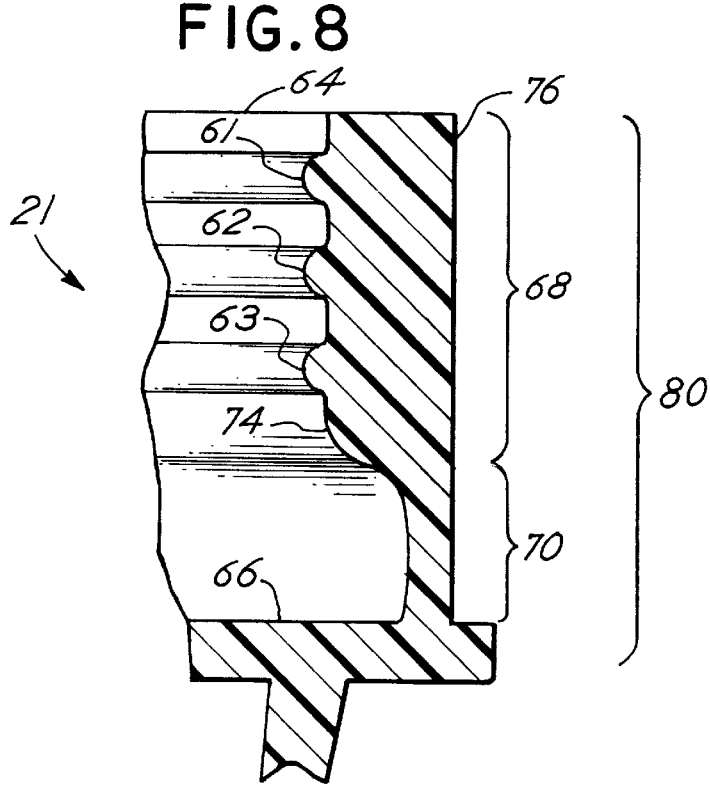
FIG. 8 is an enlarged portion of the lower cap shown in FIG. 7.

The tubular sheath portion 80 of the cap assembly has a gripping region 68 adjacent the first open end 64 of the sheath 80 that extends along an axial length of the sheath 80 and around the circumference of the sheath 80. The gripping region 68 may include at least one ridge to engage the cylindrical body 15. The preferred embodiment of the present invention shown in FIGS. 1, 5a, 5b, and 6 has five such ridges 50, 51, 52, 53, and 54. The second embodiment of the present invention shown in FIGS. 7 and 8 has three such ridges 61, 62, and 63. Ridges 50, 51, 52, 53, 54, 61, 62, and 63 extend radially inward toward the central axis 82 of the sheath 80 and around the circumference of the interior surface 74 of the sheath 80. Ridges 50, 51, 52, 53, 54, 61, 62, and 63 reduce the contact area between the gripping region 68 and the cylindrical body 15 so that the interfacial pressure may be driven up to the yield stress of the material in compression. This arrangement helps to ensure a liquid-tight seal between the cap and the cylindrical body.

The presence of multiple ridges also helps maintain an adequate seal even when the seal of one ridge is breached by a scratch or other irregularity. While two ridges may prove sufficient for this purpose, the use of more than two ridges helps to more evenly distribute the interfacial force along the inside surface of the gripping region 68. Even distribution helps prevent against sagging of the cap assembly in the area between the ridges. Sagging of the cap assembly in these regions could result in a loss of hoop tension, and hence a loss in the frictional retention forces of the cap. The preferred ridges are therefore spaced apart from one another at a distance of no more than $\frac{1}{2}\sqrt{(Rt)}$, where R is the inside radius of the gripping region 68 of sheath 80, and t is the mean wall thickness of the gripping region 68. The inside radius R and mean wall thickness t of the gripping region 68 are both measured in the radial direction.

The cap assembly of the present invention includes a transition region 70 adjacent the second end 66. This transition region 70 lies intermediate the gripping region 68 and the second end 66 of the sheath 80, and is preferably a short, thin-walled cylindrical piece having dimensions that have been calculated so as to keep the stresses accompanying the differential expansion to a level that is no higher than the stresses experienced elsewhere in the cap assembly. For example, the potential for localized discontinuities such as cracking, crazing or discoloration can be substantially reduced if neither bending nor shear strains in the transition region 70 exceed the strains in the gripping region 68. In this way the transition region 70 helps accommodate for differential expansion between the gripping region 68 and the remainder of the cap assembly to prevent against these and other undesirable discontinuities.

In particular, the transition region 70 of the preferred cap assembly has an inside radius R' and mean wall thickness t' which are both measured in the radial direction. The inside radius R' of the transition region 70 is preferably manufactured to be greater than the inside radius R of the gripping region 68, even though deformation of the cap upon receipt of a cylindrical body may change this relationship. Moreover, the axial length of the transition region 70 is, according to classical structural shell theory, preferably equal to or greater than approximately $2\sqrt{(R't')}$. While a transition region 70 that is shorter than $2\sqrt{(R't')}$ can also be used to realize the benefits of the present invention, tests have shown that the use of a transition region length that is less than approximately $0.9\sqrt{(R't')}$ will likely result in damage to the cap.

The cap of the present invention is preferably constructed from a non-elastomeric thermoplastic resin material which is injection molded. Materials having sufficient stiffness such as HDPE, LDPE, and stiff polymers such as PET and PETE, for example, may prove suitable in particular applications. It will be further understood that reinforced grades of such materials can also be used.

A thermoplastic material typically has a greater stiffness than elastomeric materials. Non-elastomeric thermoplastic materials indeed are more stiff than elastomeric materials. While components constructed from elastomeric materials may be used to easily accommodate for fairly wide variations in tolerance, the lower stiffness associated with elastomeric materials generally results in lower retention forces at the frictional fit as compared to that achieved through the use of stiffer materials such as non-elastomeric thermoplastic materials. Component geometry and material properties are carefully balanced in the preferred polypropylene cap described herein and as shown in the figures, for example, to form a cap that may be cold-assembled (without the application of heat) with tolerance to manufacturing variations, while still providing adequate in-service strength.

Figure 9:
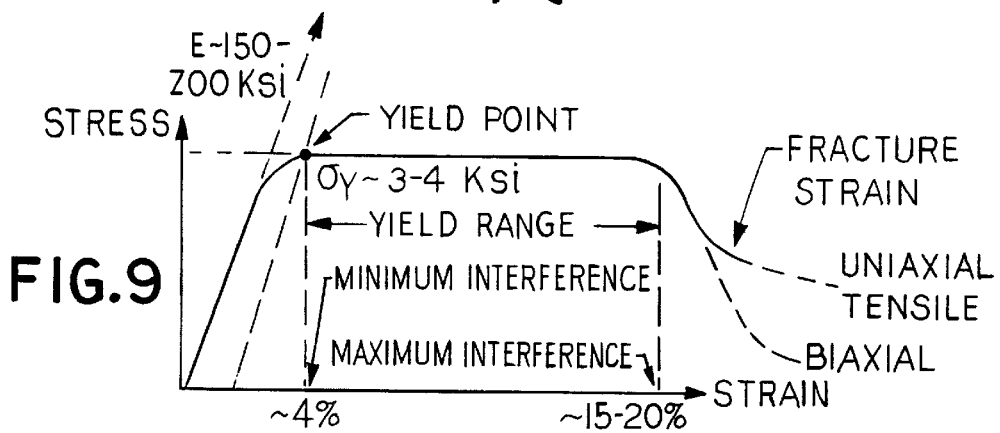
FIG. 9 is a graph depicting typical features of PP stress-strain, showing an example stress-strain plot for a polypropylene material having a yield stress value ($\sigma_y$) of approximately 3000–4000 psi and a usable yield range (maximum interference minus minimum interference) of approximately 11–16% strain.
Figure 10:
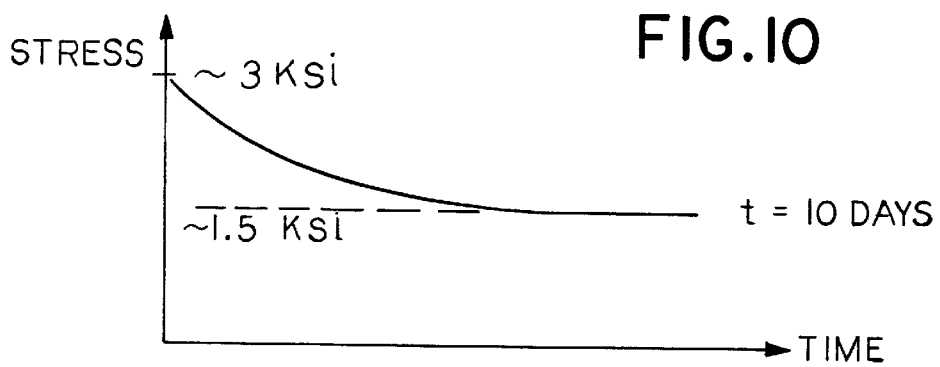
FIG. 10 is another graph depicting typical features of creep relaxation, where it is graphically shown the manner by which an initial frictional resistance or initial pull-off force may be reduced by, for example, a factor of 2 over a 10-day period, at which point a more steady-state pull-off force is maintained.

A standard stress-strain curve for a thermoplastic material is shown for example in FIG. 9. Persons of ordinary skill in the art, however, will readily understand that stress-strain characteristics vary depending on the material. Yielding occurs when a plotted curve of stress versus strain for the select material deviates noticeably from a straight line plot and begins to reach a flat plateau. For the purposes of the present invention, the yield plateau begins when the strain exceeds approximately twice the elastic strain based on the maximum stress point. At the yield plateau, increased interference causes the material to stretch at virtually constant stress, as is shown in FIG. 9.

The preferred cap assembly is designed such that each cap produced may be stretched beyond yield at room temperature during assembly for the minimum anticipated interference fit. In this way the inventive cap is less sensitive to tolerance variations of the cylindrical body. Moreover, manufacturing costs may be reduced insofar as special temperature requirements are not required for product assembly. The inventive cap simply can be secured onto the cylindrical body at room temperature.

FIG. 9 also demonstrates the ductility limits of materials, or the degree of strain that can be absorbed before the material breaks down. Material break down may manifest itself through undesirable cracks, crazes, discoloration, or other characteristics. In this way the material used in a particular application of the present invention can be limited by ductility constraints.

The yield range is preferably maximized so that the resulting caps may accommodate the widest degree of tolerance variation. In designing the cap assembly it is also important to account for the tolerance variation of both the cylindrical body and the cap itself, to help ensure that each of the resulting caps will each be stretched during assembly to a point within the yield range, for every possible combination of cap and body tolerance variations.

A 3 cc part, for example, was constructed in accordance with the present invention from a polypropylene material having a yield stress of approximately 3000 psi. The 3 cc part was designed with a transition region inside radius R' of approximately 0.231 inches and a gripping region inside radius R of approximately 0.206 inches. The mean wall thickness t' selected for the transition region was approximately 0.035 inches. This resulted in a preferred transition region length of approximately $2\sqrt{(R't')}$ ($\approx 0.180$ inches), although it was also understood that a length of approximately $0.9\sqrt{(R't')}$ ($\approx 0.078$ inches) or more would suffice. The axial length and mean thickness of the gripping region were determined as a matter of design choice to be approximately 0.265 and 0.050 inches, respectively, so as to provide the desired amount of hoop tension.

The 3 cc cap assembly described herein evidenced a reduced sensitivity to dimension variability associated with the cylindrical body 15. Indeed, the 3 cc component was designed to accommodate variations of approximately ±0.01 inches in the outside diameter of the glass tube 15 and approximately ±0.004 inches in the inside diameter of the sheath 80 without passing outside the desired yield range. Such tolerances are typical of industry standards. In this way the 3 cc component demonstrates the desired control and predictability over the resulting retention forces for a wide range of component tolerances.

Tests conducted on the 3 cc cap assembly indicate that the cap can indeed maintain a push-off force of between approximately 20 and 30 pounds when used to terminate a clean glass tube ($\mu \approx 0.2$). Specifically, when the magnitude of the frictional fit is expressed as $V=2\pi\mu T$, where $\mu$ is the coefficient of friction between the sheath 80 and the cylindrical body 15, and T is the hoop tension provided by the sheath 80, it was calculated that the 3 cc component described above provides an initial frictional resistance ($V_o$) or pull-off force of approximately 45 lbs. (calculated assuming the minimum transition region length of approximately $0.9\sqrt{(R't')}$ ). Creep relaxation in turn causes this frictional resistance to be reduced after 10 days to a more steady-state pull-off force of approximately 23 lbs.

If a silicone-coated glass tube ($\mu \approx 0.13$) is instead selected, it is calculated that the 3 cc component provides a $V_o$ of approximately 30 lbs., and a more steady-state pull-off force of approximately 15 lbs. after 10 days. However, it will be understood to those of ordinary skill in the art that by fine tuning the variables and through proper selection of the materials used it is possible to increase or decrease the level of push-off force to obtain a desired interference fit.

Indeed, it will be readily apparent to those of ordinary skill in the art that the preferred cap assembly disclosed and described herein can be modified without departing from the true spirit and scope of the invention, as defined by the claims which follow.

We claim:

1. A non-elastomeric thermoplastic cap that can be secured on a smooth end of a generally cylindrical body at room temperatures, comprising a deformable tubular sheath having an interior surface, an exterior surface, a first open end for receiving said end of said cylindrical body along a central axis of said sheath, a second end that is at least partially closed to inhibit passage of said cylindrical body through said second end, a gripping region adjacent said first open end for engaging said cylindrical body, and a transition region adjacent said second end having an inside radius (R') that is greater than an inside radius (R) of said gripping region, whereby said sheath is deformable upon interaction of said cylindrical body and said gripping region.

2. A non-elastomeric thermoplastic cap as set forth in claim 1, wherein said gripping region includes at least one ridge to engage said cylindrical body, said ridge extending radially inward toward a central axis of said sheath and around a circumference of said interior surface of said sheath.

3. A non-elastomeric thermoplastic cap as set forth in claim 2, wherein said gripping region of said sheath also has a mean thickness (t) and includes at least a first ridge and a second ridge spaced apart from one another by a distance no greater than approximately $\tfrac{1}{2}\sqrt{(Rt)}$.

4. A non-elastomeric thermoplastic cap as set forth in claim 1, wherein said generally cylindrical body is a medicant reservoir tube.

5. A non-elastomeric thermoplastic cap as set forth in claim 1, wherein said transition region of said sheath also has a mean thickness (t') and a axial length of at least approximately $2\sqrt{(R't')}$.

6. A non-elastomeric thermoplastic cap as set forth in claim 5, wherein said gripping region includes at least one ridge to engage said cylindrical body, said ridge extending radially inward toward a central axis of said sheath and around a circumference of said interior surface of said sheath.

7. A non-elastomeric thermoplastic cap as set forth in claim 6, wherein said gripping region of said sheath also has a mean thickness (t) and includes at least a first ridge and a second ridge apart from one another by a distance no greater than approximately $\tfrac{1}{2}\sqrt{(Rt)}$.

8. A non-elastomeric thermoplastic cap as set forth in claim 5, wherein said generally cylindrical body is a medicant reservoir tube.

9. A non-elastomeric thermoplastic cap as set forth in claim 8, wherein said medicant reservoir tube is a glass tube.

10. A non-elastomeric thermoplastic cap as set forth in claim 9, wherein an exterior surface of said glass tube is coated with silicone.

11. A non-elastomeric thermoplastic cap as set forth in claim 5, wherein said non-elastomeric thermoplastic cap is constructed from a polypropylene material.

12. A non-elastomeric thermoplastic cap as set forth in claim 8, wherein said cap engages said cylindrical body to maintain a frictional pull-off force of between 20 and 30 pounds.

13. A non-elastomeric thermoplastic cap as set forth in claim 12, wherein said cap is a flange member having a finger grip extending radially outward away from said central axis of said tubular sheath.

14. A non-elastomeric thermoplastic cap as set forth in claim 12, wherein said cap is a tip member having a dispensing section at said second end of said tubular sheath.

15. A non-elastomeric thermoplastic cap that can be secured on a smooth end of a generally cylindrical body at room temperatures, comprising a deformable tubular sheath having:
    an interior surface;
    an exterior surface;
    a first open end for receiving said end of said cylindrical body along a central axis of said sheath;
    a second end that is at least partially closed to inhibit passage of said cylindrical body through said second end;
    a gripping region adjacent said first open end for engaging said cylindrical body; and
    a transition region adjacent said second end having an inside radius (R') that is greater than an inside radius (R) of said gripping region, a mean thickness (t'), and an axial length of at least approximately $0.9\sqrt{(R't')}$, whereby said sheath is deformable upon interaction of said cylindrical body and said gripping region.

16. A non-elastomeric thermoplastic cap as set forth in claim 15, wherein said gripping region includes at least one ridge to engage said cylindrical body, said ridge extending radially inward toward a central axis of said sheath and around a circumference of said interior surface of said sheath.

17. A non-elastomeric thermoplastic cap as set forth in claim 16, wherein said gripping region of said sheath also has a mean thickness (t) and includes at least a first ridge and a second ridge spaced apart from one another by a distance no greater than approximately $\tfrac{1}{2}\sqrt{(Rt)}$.

18. A non-elastomeric thermoplastic cap as set forth in claim 15, wherein said generally cylindrical body is a medicant reservoir tube.

19. A non-elastomeric thermoplastic cap as set forth in claim 18, wherein said medicant reservoir tube is a glass tube.

20. A non-elastomeric thermoplastic cap as set forth in claim 15, wherein said non-elastomeric thermoplastic cap is constructed from a polypropylene material.

21. A non-elastomeric thermoplastic cap as set forth in claim 18, wherein said cap engages said cylindrical body to maintain a frictional pull-off force of between 20 and 30 pounds.

22. A non-elastomeric thermoplastic cap as set forth in claim 21, wherein said cap is a flange member having a finger grip extending radially outward away from said central axis of said tubular sheath.

23. A non-elastomeric thermoplastic cap as set forth in claim 21, wherein said cap is a tip member having a dispensing section at said second end of said tubular sheath.

24. A non-elastomeric thermoplastic cap that can be secured on a smooth end of a generally cylindrical glass medicant reservoir tube at room temperatures and maintain a frictional pull-off force of between approximately 20 and 30 pounds, comprising a deformable tubular sheath having:

an interior surface;

an exterior surface;

a first open end for receiving said end of said cylindrical tube along a central axis of said sheath;

a second end that is at least partially closed to inhibit passage of said cylindrical tube through said second end;

a gripping region adjacent said first open end for engaging said cylindrical tube, said gripping region having an inside radius (R) and a mean thickness (t), said gripping region also having at least a first ridge and a second ridge to engage said cylindrical tube, said first and second ridges extending radially inward toward a central axis of said sheath and around a circumference of said interior surface of said sheath, said first and second ridges also being spaced apart from one another by a distance no greater than approximately $\frac{1}{2}\sqrt{(Rt)}$; and a transition region adjacent said second end having an inside radius (R ') that is greater than said inside radius (R) of said gripping region, a mean thickness (t'), and an axial length of at least approximately $0.9\sqrt{(R't')}$, whereby said sheath is deformable upon interaction of said cylindrical tube and said gripping region.

25. A non-elastomeric thermoplastic cap as set forth in claim 24, wherein said non-elastomeric thermoplastic cap is constructed from a polypropylene material.

* * * * *